United States Patent [19]
Newman et al.

[11] 3,981,988
[45] Sept. 21, 1976

[54] DENTIFRICE INCLUDING A LUSTRE IMPARTING AGENT

[75] Inventors: Peter John Newman, Maidenhead; Charles Andrew Watson, Ruislip, both of England

[73] Assignee: Lever Brothers Company, New York, N.Y.

[22] Filed: Mar. 29, 1974

[21] Appl. No.: 456,330

[30] Foreign Application Priority Data
Apr. 11, 1973 United Kingdom............... 17292/73

[52] U.S. Cl.................................. 424/49; 424/154; 424/357
[51] Int. Cl.²......................................... A61K 7/16
[58] Field of Search...................... 424/49, 154, 357

[56] References Cited
UNITED STATES PATENTS

| | | | |
|---|---|---|---|
| 3,003,919 | 10/1961 | Broge | 424/49 |
| 3,227,521 | 1/1966 | Carithers | 424/49 |
| 3,670,076 | 6/1972 | Muhler | 424/49 |

FOREIGN PATENTS OR APPLICATIONS

| | | | |
|---|---|---|---|
| 1,093,139 | 11/1967 | United Kingdom | 424/49 |

Primary Examiner—James O. Thomas, Jr.
Assistant Examiner—A. P. Fagelson
Attorney, Agent, or Firm—Kenneth F. Dusyn; Arnold Grant

[57] ABSTRACT

Dentifrices containing an abrasive cleaning agent and a lustre agent impart an enhanced lustre to the teeth through the use as lustre agent of pyrogenic alumina.

3 Claims, No Drawings

DENTIFRICE INCLUDING A LUSTRE IMPARTING AGENT

This invention relates to dentifrices.

Dentifrices almost invariably contain an abrasive cleaning agent for the removal of adherent deposits on teeth. Usually the particles of the abrasive have an average particle size within the range of about 5 to about 25 microns. Examples of those abrasives which find or have found extensive commercial usage are silica xerogels, hydrated alumina, calcium carbonate, dicalcium phosphate (anhydrous and the dihydrate), insoluble sodium metaphosphate and calcium pyrophosphate.

It is desirable that after tooth cleaning the teeth should have a shiny lustrous appearance. To this end it has been proposed to include in dentifrices a more finely-divided mineral specifically to act as a tooth polishing agent. For example, in U.S. Pat. No. 3,060,098 Linde Type A alpha-alumina has been proposed for this purpose.

We have now found that a material which is particularly effective for enhancing the lustre of teeth is pyrogenic alumina (also known as fumed alumina).

Accordingly the present invention provides a dentifrice comprising an abrasive cleaning agent and a lustre agent, wherein the lustre agent is pyrogenic alumina.

The pyrogenic alumina used in this invention is made by the flame-hydrolysis process in which aluminum chloride is reacted with hydrogen and oxygen in a flame to form a very fine alumina. This form of alumina has been found to be superior as a lustre agent to Linde A alpha-alumina.

The pyrogenic alumina used in the present invention is produced as generally spherical particles having a primary particle size of about 10 to about 100 millimicrons, usually from about 10 to about 40 millimicrons, which forms aggregates. The material is substantially anhydrous, nonporous and inert. This form of alumina is predominantly of the gamma crystalline form.

The amount of the lustre-producing pyrogenic alumina incorporated in dentifrices of the invention may vary from about 0.1% to about 40% by weight, although the amount used will usually be relatively small, for instance between about 0.5% and 10% by weight.

The lustre-producing pyrogenic alumina used in this invention may be included in a wide variety of dentifrice compositions. These may be powder or liquid products but they are preferably the better known paste products extrudable from collapsible tubes or dispensed from aerosol containers. Extrudable toothpastes include the visually clear gel-like products recently introduced onto the market.

Toothpastes usually contain from about 5% to about 60% by weight of abrasive cleaning agent. The liquid phase usually comprises a mixture of water and a humectant, such as glycerol, sorbitol or propylene glycol 400 or mixtures thereof. Various other ingredients in minor amounts are conventional, particularly surface-active agent, thickener or binder and flavouring agent. Other ingredients which might also be included are anti-bacterial agents, for example 1,6-di-(p-chlorophenyl biguanido) hexane and its non-toxic acid addition salts, preservatives, sweetening agents, chloroform and titanium dioxide.

Experiments have been performed demonstrating the superior lustre-producing properties of dentifrices in accordance with the invention. The standard dentifrice used in these experiments had the following composition:

| | Weight % |
|---|---|
| Alumina trihydrate (apps 16 to 21 microns) | 54.0 |
| Sorbitol syrup (70%) | 27.0 |
| Sodium carboxymethylcellulose | 0.8 |
| Sodium lauryl sulphate | 2.0 |
| Saccharin | 0.2 |
| Flavour | 1.0 |
| Dicalcium phosphate dihydrate | 1.0 |
| Water | to 100.0 |

(aps = average particle size)

The test dentifrices used were the same as the standard product except that they contained additionally a lustre agent in place of a part of the water. Details of the various lustre agents tested are given in Table 1.

TABLE 1

| Test Dentifrice | Lustre Agent Amount | Nature |
|---|---|---|
| A | 1% | Pyrogenic alumina of average primary particle size 20 to 30 millimicrons |
| B | 2% | Flux calcined diatomite |
| C | 1% | Alpha-alumina (aps 3 microns) |
| D | 2% | Precipitated silica (aps 8 microns) |
| E | 2% | Pyrogenic silica* |
| F | 2% | Titanium dioxide |
| G | 2.5% | Alpha-alumina (aps 0.3 micron) - Linde A |

*made from silicon tetrachloride by the flame-hydrolysis method

The comparison of the lustre-producing properties of the dentifrices was carried out using a procedure which involved the measurement by means of a modified Sargrove Dental Reflectometer of the specular component of the light reflected from the surface of a tooth, previously dulled by brushing with a slurry of chalk, which had been brushed with the toothpaste under test. For each dentifrice, including the standard, there was determined the rate of change of the lustre of the tooth surface between 0 and 3,000 brush strokes. The ratio between the rate value obtained with a test product and the standard product is termed the Lustre Value for the test product. The Lustre Values obtained for the dentifrices A to G are given below in Table 2.

TABLE 2

| Test Dentifrice | Lustre Value |
|---|---|
| A | 3.1 |
| B | 2.7 |
| C | 2.1 |
| D | 1.5 |
| E | 1.0 |
| F | 0.9 |
| G | 0.5 |

The experiment showed that the test product A was clearly superior to the other test products and the standard product.

The degree of scratching produced by the test dentifrices was also determined. This was done by mechanically brushing previously polished extracted teeth for 15,000 brush strokes with a test dentifrice. The surface was then examined at a 1,000 magnification using a scanning electron microscope and the degree of scratching rated on a 1 to 4 scale, thus:

1 for unmarked surfaces
2 for slightly marked
3 for appreciably scratched
4 for severely scratched The results are given in Table 3 below.

TABLE 3

| Test Dentifrice | Scratch Rating |
| --- | --- |
| A | 2 |
| B | 3 |
| C | 4 |
| D | 2 |
| E | 1 |
| F | 3 |
| G | 4 |

This experiment showed that the test dentifrice A, as well as producing the highest degree of lustre, also resulted in only a slight degree of scratching.

Commercial dentifrice grade dicalcium phosphate is stabilised during manufacture, usually by treatment with sodium pyrophosphate and/or magnesium phosphate. The stabilised material in dentifrices does not give rise to corrosion of aluminum tubes unlike pure dicalcium phosphate. The use of finely-divided aluminum oxide for inhibiting corrosion of aluminum by dentifrices containing pure dicalcium phosphate is described in British patent specification No. 1,137,206. In as far as the following claims include the use of a dicalcium phosphate as an abrasive agent they are to be understood as extending only to the use of a stabilised material, i.e. one which is not corrosive to aluminum. The use of an unstabilised pure dicalcium phosphate is hereby disclaimed.

What is claimed is:

1. A toothpaste composition comprising in said toothpaste from about 5% to about 60% by weight of an abrasive cleaning agent having an average particle size of about 5 to about 25 microns, said abrasive cleaning agent being selected from the group consisting of silica xerogels, hydrated alumina, calcium carbonate, stabilized non-corrosive dicalcium phosphate, insoluble sodium metaphosphate and calcium pyrophosphate and a lustre agent of from about 0.1% to about 40% by weight of pyrogenic alumina, which consists predominantly of the gamma crystalline form, obtained by the flame-hydrolysis process in which aluminum chloride is reacted with hydrogen and oxygen in a flame, said alumina having a particle size of from about 10 to about 100 millimicrons.

2. The toothpaste composition of claim 1 wherein the pyrogenic alumina is present in an amount of from 0.5% to about 10% by weight and has a particle size of from about 10 to about 40 millimicrons.

3. A method of cleaning teeth and imparting a lustre thereto which comprises brushing the teeth with a sufficient amount of the toothpaste composition of claim 1 to impart said lustre.

* * * * *